US005928911A

United States Patent [19]

Saniez

[11] Patent Number: 5,928,911

[45] Date of Patent: Jul. 27, 1999

[54] METHOD FOR PRODUCING CITRIC ACID

[75] Inventor: Marie-Hélène Saniez, Saint Andre, France

[73] Assignee: Roquette Freres, Lestrem, France

[21] Appl. No.: 08/646,267

[22] PCT Filed: Sep. 20, 1995

[86] PCT No.: PCT/FR95/01209

§ 371 Date: May 21, 1996

§ 102(e) Date: May 21, 1996

[87] PCT Pub. No.: WO96/09401

PCT Pub. Date: Mar. 28, 1996

[30] Foreign Application Priority Data

Sep. 23, 1994 [FR] France .................................. 94 11388

[51] Int. Cl.[6] ............................ C12P 1/48; C07C 59/265

[52] U.S. Cl. ........................................... 435/144; 562/584

[58] Field of Search ............................ 435/144; 562/584

[56] References Cited

U.S. PATENT DOCUMENTS

| | | | |
|---|---|---|---|
| 2,492,673 | 12/1949 | Woodward et al. | 435/144 |
| 2,970,084 | 1/1961 | Schweiger et al. | 435/144 |
| 3,285,831 | 11/1966 | Swarthout et al. | 435/144 |
| 4,165,240 | 8/1979 | Enokizono et al. | 127/29 |

FOREIGN PATENT DOCUMENTS

| | | |
|---|---|---|
| 0 136 087 | 4/1985 | European Pat. Off. . |

OTHER PUBLICATIONS

J. App. Microbio, 1953, 1, 7–13 (Andrew J. Moyer).

"Starch : Chemistry and Technology" Second edition by Roy L. Whistler, pp. 491–506.

"Starch Production Technology" Radley J.A. (1976) pp. 175–187.

Prehrambeno–Tehnoloska Biotehnoloska Revija, 1994 32(1) 17–20.

"Food Acid Manufacture, Recent Developments" by A.A. Lawrence, published by Noyes Data Corp., 1974 edition pp. 2 to 74.

"Biotechnology, A Comprehensive Treatise in 8 volumes"by H.J. Rehm and G. Reed, vol. 3, Chapter 3d.

Brochures of Vogelbusch Ges. m.b.H., Austria : "Influence of Nutrient Concentration in the Fermentation Media on Production of Citric Acid By Industrially Used Strains of Aspergillus Niger".

*Primary Examiner*—Leon B. Lankford, Jr.
*Assistant Examiner*—Christopher R. Tate
*Attorney, Agent, or Firm*—Henderson & Sturm

[57] ABSTRACT

Process for the manufacture of citric acid, characterized in that at least part of the carbohydrate raw material consists of a wheat starch B hydrolysate.

6 Claims, No Drawings

METHOD FOR PRODUCING CITRIC ACID

The invention relates to a process for the manufacture of citric acid.

It also relates, by way of new industrial products, to certain raw materials which may be employed in the context of this manufacture.

Lastly, it relates to the application of certain amylaceous products to this process.

Citric acid is used mainly in the food industry, where its pleasant acid taste and its great solubility make it liked especially in drinks, jams and sweetmeats, but it is also used in the pharmaceutical and cosmetics industries and in the plastics and detergent industries.

Citric acid is now obtained almost exclusively by fermentation processes employing fermentation of various carbohydrates-based substrates in deep vats.

The microorganisms capable of producing and accumulating citric acid can belong to the Aspergillus, Citromyces, Penicillium, Monilia, Candida and Pichia species. The black Aspergillus species, and especially *Aspergillus niger,* are employed in particular in this type of production. The most effective strains are those which possess low isocitrate dehydrogenase and aconitate hydratase activities and high citrate synthase activity. These strains all have in common the feature of being very sensitive to traces of heavy metals.

The carbohydrates which are employed in these processes can be more or less refined. However, their state of purity gives rise to different constraints.

Thus, food grade crystallized sucrose or dextrose does not contain heavy metals. They furnish yields of citric acid greater than 70% but are expensive.

However, the recovery of the citric acid is greatly facilitated by the purity of such substrates.

Cane or beet molasses are cheap substrates. However, the large amount of impurities they contain create huge problems of treatment of the heavy metals and of purification of the citric acid.

Starch hydrolysates are a little more expensive than molasses. Irrespective of whether they are from maize, wheat, potato or rice, they contain less impurities than molasses and the purification of the citric acid is thereby facilitated. However, their use is limited because these substrates which have undergone little purification also contain substances of unknown nature which increase the adverse effects of heavy metals on citric fermentation.

It is thought that these substances which potentiate the effect of heavy metals, which are essentially iron, manganese and zinc, may be amino acid residues, peptides, enzymes or intermediate metabolites. Conversely, some substances which stimulate citric fermentation have sometimes been detected, although their chemical nature has not been clarified.

Methods exist which make it possible to combat the adverse effect on citric fermentation of the heavy metals present in substrates which have undergone little purification.

For example, they may be complexed using hexacyanoferrate, or their effects may be counteracted by adding copper.

MOYER (J. App. Microbio 1, 7–13), using an *Aspergillus niger* strain endowed with amylolytic properties, demonstrated that an unhydrolyzed native wheat starch could also be fermented successfully to citric acid by neutralizing the effect of heavy metals by adding an alcohol.

SWARTHOUT (U.S. Pat. No. 3,285,831) employed an enzyme hydrolysate of a crude maize flour to obtain citric acid by the action of *Aspergillus niger.* He got rid of heavy metals by trapping them on a cation exchange resin, and also suggested treating a wheat flour enzyme hydrolysate in the same way. Such hydrolysates obtained from whole cereal flours contain, however, a large amount of impurities, and in particular a large amount of proteins which interfere with the final recovery of the citric acid.

However, a cheaper substrate which is sufficiently pure not to cause problems of recovery of the citric acid or of removal of heavy metals, and which contains, furthermore, substances which stimulate citric fermentation, has not yet been identified or turned to good account.

It is to the credit of the Applicant Company that it recognized such a substrate in a hydrolysate of a by-product of wheat starch manufacture, commonly known as starch B. Surprisingly, such a substrate enables much higher productivities and yields to be obtained than is possible using a hydrolysate obtained from a purer starch such as wheat starch A or a maize starch, for example.

In addition, the fact of employing a starch hydrolysate rather than a native starch, as done by MOYER, permits higher productivities, since the rate of fermentation is not limited by the amylolytic potential of the Aspergillus strains employed.

Starch B or second starch consists essentially of a preponderant proportion of small starch granules or of damaged granules, and contains impurities such as pentosans, proteins and lipids.

These impurities in wheat starch B, some of which elude the traditional purification and demineralization treatments, are to be found in the hydrolysates of these starches, and make starch B unsuitable, for example, for the manufacture of food grade dextrose. It is thus difficult for such starches B to find industrial outlets.

However, and this is the feature underlying its invention, the Applicant Company has discovered that these impurities possess a beneficial effect on citric acid fermentation, thereby affording this by-product a new industrial outlet.

Starch B is obtained in the proportion of approximately 6 to 17 kg of starch per quintal of wheat flour employed in starch manufacture, while the purer starch A, essentially composed of large starch granules, is obtained in a proportion of approximately 55 to 65 kg of starch per quintal of wheat flour employed. Only this grade of wheat starch has until now found superior applications.

An account of the processes currently employed in wheat starch manufacture will be found in the work: "STARCH: Chemistry and Technology" edited by ROY L. WHISTLER, pages 491 to 506 of the second edition, or alternatively in the work "Starch Production Technology", RADLEY J. A. (1976), pp. 175 to 187 and page 178 in particular.

As a guide, a comparative chemical analysis of wheat starches A and B as these latter may be found on the market will be found in the table below.

In any case, wheat starch B, in the sense generally accepted by the trade and which is the one applied to it by the Applicant, contains more than 90% of starch and less than 5% of protein.

Hence the product in question cannot be confused with the residue having a low dry matter content and containing less than 70% of starch which has been dehydrated and then hydrolysed to serve as a substrate for the citric fermentation described in PREHRAMBENO-TEHNOLOSKA BIOTEHNOLOSKA REVIJA, 1994, 32 (1) 17–20. Such a substrate furnishes, moreover, only mediocre yields of citric acid, and is in reality the final residue of wheat starch manufacture comprising, besides starch, the bulk of the soluble matter of wheat flour (pentosans and sugars).

| | STARCH A | STARCH B |
|---|---|---|
| Loss on drying | 13% | 13% |
| Proteinaceous matter (N × 6.25) | 0.35% | 0.7 to 2% |
| Soluble matter | <1% | 1 to 3% |
| Reducing sugars | <0.5% | 0.5 to 3% |
| Starch | not less than 97% | approx. 93% |
| Residue on ignition | <0.5% | 1% |
| Pentosans | trace | 1.5% |
| Lipids | 0.5% | 1% |
| 80% by weight of the granules | >10 microns | <8.4 microns |

It follows that the process for the manufacture of citric acid according to the invention is characterized in that at least part of the carbohydrate raw material employed for the fermentation consists of a wheat starch B hydrolysate. Preferably, this hydrolysate represents at least 25% of the carbohydrate raw material employed, more preferably it represents at least 50% thereof and still more preferably at least 75% thereof.

Starch hydrolysate is understood here to mean hydrolysates in which the true glucose content amounts to 85% and more of the carbohydrate fraction of these hydrolysates. Such hydrolysates can be obtained only with wheat starches B assaying a starch content of at least 90%. Preferably, this true glucose content is greater than 90%, and still more preferably it is greater than 92%. There may be obtained by the acid hydrolysis of starch, but are preferably obtained by the action of amylolytic enzymes such as alpha-amylase, amyloglucosidase, isoamylase or pullulanase.

Such hydrolysates may be used in the process of the invention employing techniques of neutralization of the heavy metals with hexacyanoferrate or with methanol, for example, but, according to an advantageous embodiment of the abovementioned process, it is preferable to use a starch hydrolysate obtained exclusively on the basis of wheat starch B and from which the majority of the heavy metals have been removed by demineralization on a strong cation exchange resin converted into its hydrogen form or, where appropriate, its alkali metal or alkaline-earth metal form.

As new industrial products, the invention relates to wheat starch B hydrolysates which are characterized in that they contain less than 500 ppb (parts per billion) of iron and less than 20 ppb of manganese, these contents being expressed relative to the dry matter of the hydrolysates.

Such starch B hydrolysates according to the invention may be marketed in the state of syrups demineralized on cation exchange resin and then concentrated, on condition that the majority of the anions have been removed, or that the acidity introduced by the cation exchange resins has been corrected by neutralizing it at least partially by means of a non-toxic base such as sodium hydroxide, potassium hydroxide or ammonia solution.

The latter base possesses, in addition, the advantage of supplying part of the nitrogen needed for fermentation.

This problem of neutralization of acidity does not arise if the cation exchange resins are used in this ammoniacal form. Such neutralization precautions are necessary because it is known that, in a hot, acid and concentrated medium, glucose can polymerize to form oligosaccharides which are difficult to ferment.

To obtain the wheat starch hydrolysates to be employed in the process of the invention, the procedure which follows or an equivalent procedure may be used.

Liquefaction of a starch milk containing at least 25% of wheat starch B is first obtained by the action of a heat-stable alpha-amylase such as the enzyme TERMAMYL marketed by the company NOVO. This liquefaction is generally performed at a temperature of between 65° C. and 110° C., at a pH of between 5.5 and 6.5, with a dry matter content of between 5% and 45%, for a time of 1 to 3 hours, with a dose of enzyme representing from 24 KNU units (Kilo Novo Units) to 240 KNU units per kilogram of wheat starch, until a DE (dextrose equivalent) of between 5 and 20 is obtained.

Saccharification of this liquefied wheat starch is then obtained by the action of a fungal amyloglucosidase preferably, such as the enzyme DEXTROZYME also marketed by the company NOVO.

Other enzymes such as pullulanase, isoamylase or enzymes for the hydrolysis of hemicelluloses may also be added. This saccharification is generally performed at a temperature of between 55° C. and 63° C., at a pH of between 3.5 and 5.5, with a dry matter content of between 5% and 45%, for a time of 20 to 90 hours, with a dose of enzyme representing from 60 GAU units (glucose amyloglucosidase units) to 500 GAU units per kilogram of starch, until a Dx (true glucose percentage) of at least 85% is obtained.

When saccharification is complete, it is preferable to filter the hydrolysates, and they may be decolorized and concentrated as is standard practice in the starch manufacturing industry.

The wheat starch hydrolysate thereby obtained proves to be a substrate especially well suited to the production of citric acid by means of fermentation using *Aspergillus niger*, especially if this hydrolysate is prepared on the basis of least 25% of wheat starch B.

It may be used as it is, neutralizing the heavy metals it contains with hexacyanoferrate or alcohol or by adding copper, but it is preferable to use a wheat starch B hydrolysate which has been subjected to a treatment on strong cation exchange resin in order to lower its iron content to less than 500 ppb and its manganese content to less than 20 ppb, so as to obtain the product of the invention. It is apparent that this approach is the one which enables best use to be made of the substances which stimulate citric fermentation, contained in the impurities of wheat starches B.

To this end, the resins used are generally of the type having a polystyrene skeleton, crosslinked with divinylbenzene and functionalized by sulphonation. Such resins are items commonly available on the market. Examples include the resin C 150 marketed by PUROLITE, or alternatively the resin C 200 marketed by ROHM and HAAS, or alternatively the resin CM 12 marketed by DOW CHEMICALS.

These resins are employed under the traditional demineralization or exchange conditions recommended by their manufacturers.

Use of the wheat starch B hydrolysate according to the invention, as carbohydrate substrate intended for the manufacture of citric acid, is made in accordance with the general body of knowledge of a person skilled in the art, as is gathered, for example, in the work "FOOD ACID MANUFACTURE, Recent Developments" by A. A. LAWRENCE, published by NOYES DATA Corp., 1974 edition, pages 2 to 74, or alternatively in the work entitled "BIOTECHNOLOGY, A Comprehensive Treatise in 8 Volumes", edited by H. J. REHM and G. REED, Volume 3, Chapter 3d, or alternatively in the brochures of the company VOGELBUSCH Ges. m.b.H., Austria: "INFLUENCE OF NUTRIENT CONCENTRATION IN THE FERMENTATION MEDIA ON PRODUCTION OF CITRIC ACID BY INDUSTRIALLY USED STRAINS OF *ASPERGILLUS NIGER*".

Generally speaking, the fermentations are conducted in deep, aerated vats at glucose concentrations of between 120 and 200 grams per liter. Even in the case of substrates demineralized by ion exchange, it is preferable to employ a little copper and zinc which can inhibit the iron or manganese which might be extracted from the metal parts of the fermenters during fermentation or which escape in the state of traces from the resins. The only nutrients added are generally nitrogenous, preferably in ammonium form. In effect, in the case of the fermentation of hydrolysates essentially prepared on the basis of wheat starch B, their content of phosphorus-containing impurities is generally such that it is not necessary to add phosphates to the culture musts. The fermentations are conducted at a pH slightly below 2.0 at approximately 30° C. for 5 to 8 days until the reducing sugars have almost completely disappeared. Inoculation of the fermenters is generally effected with a suspension of *Aspergillus niger* spores or germinated spores.

The object of the examples which follow is to provide a better illustration of the invention which has just been described. Their aim is especially to demonstrate the surprising and unexpected differences which are seen in the behaviours of wheat starch A and B hydrolysates, with respect to citric fermentation by *Aspergillus niger* in general. This difference in behaviour is illustrated here by an *Aspergillus niger* strain suited to the fermentation of glucose.

EXAMPLES

Wheat starches A and B, obtained from the same variety of wheat according to a process similar to the MARTIN process as described in broad outline in the work "STARCH: Chemistry and Technology" edited by R. L. WHISTLER, second edition 1984, on pages 495–497, were hydrolysed under the following identical conditions:

liquefaction by TERMAMYL brand alpha-amylase marketed by NOVO, in the proportion of 0.1% by weight of enzyme per kilo of dry starch, corresponding to 120 KNU per Kg of starch, under the following conditions:

pH=6.2 temperature=96° C.

time=2 h to a DE value of 15.5. This is followed by saccharification with DEXTROZYME amyloglucosidase in the proportion of 0.085 0/0 of enzyme per kilo of starch under the following conditions:

pH 4.5 temperature 60° C.

time 60 hours.

The syrups obtained were both filtered through diatomaceous earth and then demineralized on a C 200 cation exchange resin marketed by the company ROHM and HAAS and regenerated in its hydrogen form.

The wheat starch hydrolysates thereby obtained showed a carbohydrate composition displaying hardly any difference, since they were established as being as follows:

| | STARCH A HYDROLYSATE | STARCH B HYDROLYSATE |
|---|---|---|
| Glucose | 94% | 93.3% |
| Disaccharides | 4.1% | 4.2% |
| Trisaccharides | 0.8% | 0.6% |
| Tetrasaccharide and higher | 0.8% | 1.4% |
| Fructose | 0.3% | 0.2% |

Their heavy metal content was very low, since it was established as being less than 500 ppb of iron and less than 20 ppb of manganese.

Fermentation of these carbohydrate substrates was conducted in "bubble column" type glass fermenters equipped with pH probes, pH regulation, foam control and a system designed to compensate for losses due to evaporation.

These fermenters have a useful volume of 8.5 liters for a total volume of 17 liters. Temperature control is effected by a water bath.

The demineralized wheat starch hydrolysates are sterilized beforehand in glass bottles by heating for 30 minutes with live steam.

The fermenters are also sterilized with live steam for approximately 90 minutes and are then cooled by blowing sterile air into them.

The dilution water is introduced into the fermenters via a sterile 0.2 micrometer membrane filter. This water has been demineralized beforehand.

The sterilized hydrolysates and a sterile solution of nutrient salts are then added so that the culture musts contain (per liter of must):

25 ppm of $Mg^{++}$ 60 ppm of $Ca^{++}$ 100 ppm of $K^{+}$ 150 ppb of $Fe^{++}$ 500 ppb of $Cu^{++}$ 400 ppb of $Zn^{++}$ The phosphate concentration of the wheat starch B hydrolysates demineralized on cation exchange resin is sufficient to provide for correct growing [sic] of the mycelium.

The pH of the culture musts is then brought to 3.5 by adding 25% ammonia solution and is thereafter adjusted to pH 1.8 by adding this same ammonia solution throughout the fermentation.

Inoculation is carried out using a suspension of spores of a strain derived from Aspergillus niger ATCC 11414 which is accustomed to fermenting glucose.

The inoculation ratio is 0.7 mg of spores per liter of must to be fermented.

The fermenter temperature is maintained at 30° C. during the phase of production of citric acid. It can be higher at the time of inoculation so as to obtain a faster germination of the spores. The fermenters were aerated at a flow rate of 70 l/min during the first sixteen hours and then at a flow rate of 90 l/min throughout the fermentation.

Samples were removed regularly throughout the fermentations, and the latter were terminated when the residual glucose level was below 2 g/l. Whether they came from a wheat starch A (comparative examples) or a starch B (examples according to the invention), the substrates were tested at various initial concentrations, and the most representative results have been collated in the table below.

The initial glucose concentrations of the culture musts, the total fermentation time, the final citric acid concentration after correction for losses due to evaporation, the final biomass content of the musts, the productivity obtained in grams of citric acid monohydrate per liter of must per hour and the weight yield of citric acid monohydrate relative to the glucose employed appear in this table.

| | Substrate Hydrolysate of wheat starch | Initial Glc. g/l | Production time (h) | Citric acid (g/l) | Biomass (g/l) | Productivity (g/l/h) | Yield (%) |
|---|---|---|---|---|---|---|---|
| Comparative | A | 125 | 137 | 91 | 12 | 0.67 | 72.5 |
| Examples | A | 147 | 155 | 98 | 15 | 0.64 | 68.5 |
| Examples | B | 140 | 132 | 104 | 15.4 | 0.79 | 74 |
| according to | B | 173 | 115 | 128.7 | 19.6 | 1.12 | 74 |
| the invention | B | 176 | 123 | 137 | 18.7 | 1.11 | 78 |

It was found that, by increasing the glucose content to values above 120 g/l, a concomitant fall was obtained in the yield and productivity when the substrate consisted of a wheat starch A hydrolysate.

In contrast, it is found that the process and wheat starch B hydrolysate according to the invention enable enhanced productivities and yields of citric acid to be obtained surprisingly and without the reason for this being understood, and this phenomenon becomes increasingly pronounced as the glucose concentration of the culture musts is increased to values close to 180 grams per liter.

Mixed hydrolysates of wheat starch A and B yield intermediate results which confirm that wheat starches B or wheat starch B hydrolysates contain substances which stimulate citric fermentation.

Similarly, wheat starch B hydrolysates employed as a mixture with maize starch hydrolysates substantially increase the productivities and concentrations, and to a lesser extent the yields, of citric acid which are possible to obtain from hydrolysates originating from maize starch, which is much purer than wheat starch B.

These wheat starch B hydrolysates thus find an especially advantageous use as an agent for increasing the productivity, concentration and yield of citric acid, as all or part of the carbohydrate substrate to be fermented.

I claim:

1. A process for the manufacture of citric acid, said process comprising treating a carbohydrate raw material under conditions effective to produce citric acid and recovering said citric acid, whereby at least 25% of the carbohydrate raw material employed consists of a wheat starch B hydrolysate wherein the carbohydrate fraction of the wheat B hydrolysate contains at least 85% glucose.

2. The process according to claim 1, whereby the wheat B hydrolysate represents at least 50% of the carbohydrate raw material employed.

3. The process according to claim 1, whereby the wheat B hydrolysate represents at least 75% of the carbohydrate raw material employed.

4. An industrial product for use in manufacturing citric acid consisting of a wheat starch B hydrolysate in which the carbohydrate fraction therein contains at least 85% glucose, said hydrolysate having undergone treatment on a cation exchange resin, and which contains less than 500 ppb of iron and less than 20 ppb of manganese.

5. The industrial product according to claim 4, wherein the carbohydrate fraction of the wheat B hydrolysate contains at least 90% glucose.

6. The industrial product according to claim 4, wherein the carbohydrate fraction of the wheat B hydrolysate contains at least 92% glucose.

* * * * *